US010758409B2

(12) United States Patent
Franco et al.

(10) Patent No.: US 10,758,409 B2
(45) Date of Patent: Sep. 1, 2020

(54) APPARATUS AND METHOD FOR TREATING EYE DISEASES

(71) Applicant: Ocudyne LLC, Plano, TX (US)

(72) Inventors: Jeff Franco, Plano, TX (US); Michael Calhoun, Lighthouse Point, FL (US)

(73) Assignee: J.D. Franco & Co., LLC, Plano, TX (US)

( * ) Notice: Subject to any disclaimer, the term of this patent is extended or adjusted under 35 U.S.C. 154(b) by 207 days.

(21) Appl. No.: 15/636,532

(22) Filed: Jun. 28, 2017

(65) Prior Publication Data

US 2018/0140460 A1   May 24, 2018

Related U.S. Application Data

(63) Continuation of application No. PCT/US2015/067939, filed on Dec. 29, 2015.

(Continued)

(51) Int. Cl.
| A61F 9/007 | (2006.01) |
| A61F 2/856 | (2013.01) |
| A61F 2/90 | (2013.01) |
| A61F 2/95 | (2013.01) |
| A61F 2/07 | (2013.01) |
| A61F 2/966 | (2013.01) |

(Continued)

(52) U.S. Cl.
CPC .............. *A61F 9/007* (2013.01); *A61F 2/07* (2013.01); *A61F 2/856* (2013.01); *A61F 2/90* (2013.01); *A61F 2/95* (2013.01); *A61F 2/966* (2013.01); *A61F 9/0017* (2013.01); *A61F 2002/061* (2013.01); *A61F 2002/821* (2013.01); *A61F 2210/0004* (2013.01); *A61F 2250/0039* (2013.01); *A61F 2250/0067* (2013.01); *A61F 2250/0098* (2013.01)

(58) Field of Classification Search
CPC .. A61F 2/856; A61F 2002/821; A61F 9/0017; A61F 9/007; A61F 9/00709; A61F 9/00781
See application file for complete search history.

(56) References Cited

U.S. PATENT DOCUMENTS

| 2,690,595 A | 10/1954 | Raiche |
| 3,367,101 A | 2/1968 | Garnet et al. |

(Continued)

FOREIGN PATENT DOCUMENTS

| WO | WO 98/52639 A1 | 11/1998 |
| WO | WO 98/53761 A1 | 12/1998 |

(Continued)

OTHER PUBLICATIONS

Altinbas, N.K. et al, "Effect of Carotid Artery Stenting on Ophthalmic Artery Flow Patterns," Journal of Ultrasound Medicine, 2014; 33: pp. 629-638.

(Continued)

*Primary Examiner* — Ryan J. Severson
(74) *Attorney, Agent, or Firm* — Bookoff McAndrews, PLLC

(57) ABSTRACT

A method, device, or system for treating eye disorders or conditions, comprising restoring or increasing blood flow or blood flow rate in an artery that supplies blood to or in the eye, thereby increasing the amount of oxygen that reaches the eye or a portion thereof.

20 Claims, 4 Drawing Sheets

Related U.S. Application Data

(60) Provisional application No. 62/148,701, filed on Apr. 16, 2015, provisional application No. 62/137,789, filed on Mar. 24, 2015, provisional application No. 62/097,552, filed on Dec. 29, 2014, provisional application No. 62/097,554, filed on Dec. 29, 2014, provisional application No. 62/097,556, filed on Dec. 29, 2014.

(51) Int. Cl.
*A61F 9/00* (2006.01)
*A61F 2/82* (2013.01)
*A61F 2/06* (2013.01)

(56) References Cited

U.S. PATENT DOCUMENTS

| | | |
|---|---|---|
| 3,435,826 A | 4/1969 | Fogarty |
| 4,403,612 A | 9/1983 | Fogarty |
| 4,926,858 A | 5/1990 | Gifford, III et al. |
| 5,026,384 A | 6/1991 | Farr et al. |
| 5,176,693 A | 1/1993 | Pannek, Jr. |
| 5,395,311 A | 3/1995 | Andrews |
| 5,709,701 A | 1/1998 | Parodi |
| 5,820,595 A | 10/1998 | Parodi |
| 5,897,567 A | 4/1999 | Ressemann et al. |
| 6,146,370 A | 11/2000 | Barbut |
| 6,206,868 B1 | 3/2001 | Parodi |
| 6,302,908 B1 | 10/2001 | Parodi |
| 6,336,933 B1 | 1/2002 | Parodi |
| 6,344,054 B1 | 2/2002 | Parodi |
| 6,413,235 B1 | 7/2002 | Parodi |
| 6,423,032 B2 | 7/2002 | Parodi |
| 6,540,712 B1 | 4/2003 | Parodi et al. |
| 6,623,471 B1 | 9/2003 | Barbut |
| 6,641,573 B1 | 11/2003 | Parodi |
| 6,645,222 B1 | 11/2003 | Parodi et al. |
| 6,824,558 B2 | 11/2004 | Parodi |
| 6,827,726 B2 | 12/2004 | Parodi |
| 6,837,881 B1 | 1/2005 | Barbut |
| 6,855,162 B2 | 2/2005 | Parodi |
| 6,902,540 B2 | 6/2005 | Dorros et al. |
| 6,905,490 B2 | 6/2005 | Parodi |
| 6,908,474 B2 | 6/2005 | Hogendijk et al. |
| 6,929,634 B2 | 8/2005 | Dorros et al. |
| 6,936,053 B1 | 8/2005 | Weiss |
| 6,936,060 B2 | 8/2005 | Hogendijk et al. |
| 7,214,201 B2 | 5/2007 | Burmeister et al. |
| 7,235,095 B2 | 6/2007 | Haverkost et al. |
| 7,309,334 B2 | 12/2007 | Von Hoffmann |
| 7,604,612 B2 | 10/2009 | Ressemann et al. |
| 7,867,273 B2 | 1/2011 | Pappas et al. |
| 7,901,445 B2 * | 3/2011 | Wallace ............ A61B 17/12118 623/1.11 |
| 7,927,347 B2 | 4/2011 | Hogendijk et al. |
| 8,157,760 B2 | 4/2012 | Criado et al. |
| 8,353,850 B2 | 1/2013 | Ressemann et al. |
| 8,545,432 B2 | 10/2013 | Renati et al. |
| 8,834,404 B2 | 9/2014 | Beaudin |
| 8,852,226 B2 | 10/2014 | Gilson et al. |
| 8,863,631 B1 | 10/2014 | Janardhan et al. |
| 9,078,682 B2 | 7/2015 | Lenker et al. |
| 9,241,699 B1 | 1/2016 | Kume et al. |
| 9,259,215 B2 | 2/2016 | Chou et al. |
| 9,265,512 B2 | 2/2016 | Garrison et al. |
| 2001/0001114 A1 | 5/2001 | Tsugita et al. |
| 2002/0087128 A1 | 7/2002 | Paques et al. |
| 2002/0151922 A1 | 10/2002 | Hogendijk et al. |
| 2003/0023200 A1 | 1/2003 | Barbut et al. |
| 2003/0023227 A1 | 1/2003 | Zadno-Azizi et al. |
| 2003/0199802 A1 | 10/2003 | Barbut |
| 2003/0199819 A1 | 10/2003 | Beck |
| 2003/0203958 A1 | 10/2003 | Kunz et al. |
| 2005/0149117 A1 | 7/2005 | Khosravi et al. |
| 2006/0136022 A1 | 6/2006 | Wong, Jr. et al. |
| 2006/0259132 A1 * | 11/2006 | Schaffer ............ A61F 2/82 623/1.49 |
| 2008/0027519 A1 | 1/2008 | Guerrero |
| 2008/0243229 A1 * | 10/2008 | Wallace ............ A61B 17/12118 623/1.15 |
| 2009/0018455 A1 | 1/2009 | Chang |
| 2009/0024072 A1 | 1/2009 | Criado et al. |
| 2009/0030323 A1 | 1/2009 | Fawzi et al. |
| 2010/0125244 A1 | 5/2010 | McAndrew |
| 2011/0143993 A1 | 6/2011 | Langer et al. |
| 2011/0152683 A1 | 6/2011 | Gerrans et al. |
| 2011/0160762 A1 | 6/2011 | Hogendijk et al. |
| 2011/0274748 A1 * | 11/2011 | Robinson ............ A61K 31/4192 424/450 |
| 2012/0046679 A1 | 2/2012 | Patel et al. |
| 2012/0078287 A1 | 3/2012 | Barbut |
| 2012/0101510 A1 | 4/2012 | Lenker et al. |
| 2013/0197621 A1 | 8/2013 | Ryan et al. |
| 2013/0281788 A1 | 10/2013 | Garrison |
| 2014/0154246 A1 * | 6/2014 | Robinson ............ A61K 31/4192 424/133.1 |
| 2015/0313607 A1 | 11/2015 | Zhadkevich |
| 2015/0366580 A1 | 12/2015 | Lenihan et al. |
| 2016/0166754 A1 | 6/2016 | Kassab et al. |

FOREIGN PATENT DOCUMENTS

| | | |
|---|---|---|
| WO | WO 00/54673 A1 | 9/2000 |
| WO | WO 03/018085 A2 | 3/2003 |
| WO | WO 2007/103464 A2 | 9/2007 |
| WO | WO 2014/022866 A1 | 2/2014 |
| WO | WO 2016/109586 A1 | 7/2016 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

(56) References Cited

OTHER PUBLICATIONS

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P.F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/051551, dated Dec. 15, 2017 (14 pages).

International Search Report and Written Opinion for International Application No. PCT/US2017/052901, dated Dec. 8, 2017 (9 pages).

Hayreh et al., "Ocular Arterial Occlusive Disorders and Carotid Artery Disease," American Academy of Ophthalmology, 2017; vol. 1, No. 1: pp. 12-18.

Hayreh et al., "The Ophthalmic Artery," Brit. J. Ophthal., 1962; 46, 65: pp. 65-98.

\* cited by examiner

APPARATUS AND METHOD FOR TREATING EYE DISEASES

This application is a continuation of International Patent Application No. PCT/US15/67939 filed Dec. 29, 2015; which claims the benefit of U.S. Patent Application No. 62/148,701 filed Apr. 16, 2015, U.S. Patent Application No. 62/137,789 filed Mar. 24, 2015, U.S. Patent Application No. 62/097,554 filed Dec. 29, 2014, U.S. Patent Application No. 62/097,552 filed Dec. 29, 2014 and U.S. Patent Application No. 62/097,556 filed Dec. 29, 2014.

FIELD OF THE INVENTION

The present invention relates to treating eye diseases and conditions. The present invention also relates to stents and their use in the treatment of eye disorders.

BACKGROUND OF THE INVENTION

Diseases of the eye, specifically age-related macular degeneration (AMD), glaucoma and diabetic retinopathy affect a large percentage of the population. In the example of AMD, currently approved treatments include surgically implanting a miniature lens (VisionCare), monthly injections of the anti-cancer drug Avastin into the eye, injecting a therapeutic antibody into the eye (Macugen, pegaptanib), and/or photo or laser treatment to destroy "abnormal" blood vessels. However, these therapies are deficient in one or more aspects, necessitating improved approaches. In part, most of the diseases of the eye are treated by treating one or more symptoms, but failing to address the underlying cause(s) of the disease or condition.

In a general sense, the pathogenesis of some of these eye diseases and conditions is similar if not the same as those seen for cardiac diseases and for abdominal aorta conditions. However, the anatomy of the vasculature behind the eye is typically smaller, includes more branches, and includes more odd angles in the blood flow pathway, e.g., the angle where one artery meets or joins another is sometimes quite severe.

While not intending to be restricted to any particular theory of operation, function, or causal connection, the inventors believe any condition that leads to lowered oxygen delivery to the tissue in and around the eye mediates and/or causes any of a variety of eye diseases, including but not limited to AMD. Possible conditions include but are not limited to one or more of the following: blockage in the internal carotid artery; blockage in the ophthalmic artery; reduced blood flow anywhere in the fluid flow path between the ICA and eye tissue; reduced blood flow rate anywhere in the fluid flow path between the ICA and eye tissue; decreased hemoglobin amount or delivery to one or more eye tissues; and blockage or reduced flow in any of the junctions or ostia between any of the vasculature between the ICA and one or more eye tissues.

The general anatomical area of interest is all of the vasculature that is in the fluid flow path to and from the eye, the rear of the eye, portions of the eye, or regions near the eye. The primary areas of the anatomy include, but are not limited to the Internal Carotid Artery (ICA), the Ophthalmic Artery (OA) and the junction between the ICA and the OA, which is referred to in this disclosure as the ostium. Secondary areas of the anatomy include the vascular system commonly referred to as the terminal branches. These areas include, but are not limited to the Supra orbital Artery (SOA), the Supra Trochlear Artery (STA), the dorsal Nasal Artery (DNA), and the facial Arteries (FA).

Medically and therapeutically, there are also zones of interest: Zone 1 includes the ICA above and below the OA ostium (including the ostium itself); Zone 2 includes the OA from the ostium to the annulus of Zinn; and Zone 3 includes the annulus of Zinn to the terminal OA arteries.

BRIEF SUMMARY OF THE INVENTION

The present invention addresses some or all of the problems found in current therapies by focusing one or more therapies or processes on a key feature of most eye-related dysfunctions—decreased oxygen to and around the eye, believed to be involved in blood flow to, in, and around the eye. The inventors believe that decreased oxygen, regardless of the cause and even to the point of hypoxia, may be involved or implicated in many eye diseases or conditions.

The present invention includes methods and devices for restoring or increasing the amount of oxygen that reaches the eye or eye area. Restoring or increasing refers to removing or opening a blockage (or partial blockage) in one or more of vascular systems that support the eye. Opening a blockage or partial blockage refers to increasing or restoring blood flow to or around the eye. As used herein, increasing blood flow includes but is not limited to increasing the blood flow rate.

The present invention includes methods for percutaneous access and treatment of vascular structures at the rear of the eye, intended to provide devices and treatment methods for diseases of the eye related to compromised vascular flow. These methods include, but are not limited to, treatment for the symptoms related to Age Related Macular Degeneration, Glaucoma and Diabetic Retinopathy by placement of a stent in the ICA/OA ostium to provide treatment to stenosis in Ophthalmic/Internal Carotid Artery (ICA/OA) ostium, thereby restoring normal, near normal or improved blood flow to the rear of the eye, including the retina, choroid and/or associated structures The present invention also provides one or more stents positioned in the vasculature supplying blood to the eye, and a stent that is specifically designed for placement in the Internal Carotid Artery (ICA), will reduce the likelihood of thrombotic events due to ICA plaque disruption, places specific support in the ICA/Ophthalmic Artery (OA) ostium to provide patency and is designed with radiopaque features to guide in accurate placement.

In accordance with the present invention, diseases and conditions of the eye may be directly mediated by compromised blood flow to the vasculature of the posterior eye.

The present invention is also directed to one or more intravascular medical devices and methods intended to sufficiently unblock or partially restore blood flow in a blocked or partially blocked artery such that oxygen content is increased distal to the blockage. An embodiment of the invention is directed to devices and methods for restoring blood flow through the ostium. An embodiment of the invention includes using these devices and methods to restore or increase blood flow to the eye or a portion thereof. An embodiment of the invention includes restoring or increasing oxygen levels in the eye or a portion thereof. Restoring or increasing oxygen flow may include using these devices and methods, or equivalent devices and methods, but is not to be limited thereby.

The use of catheter delivery systems for positioning and deploying therapeutic devices, such as balloons, stents and embolic devices, in the vasculature of the human body has become a standard procedure for treating endovascular diseases. It has been found that such devices are particularly useful in treating areas where traditional operational procedures are impossible or pose a great risk to the patient. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

The initial disease target is Age-Related Macular Degeneration (AMD). In AMD, we believe lack of blood flow to the posterior eye vasculature directly reduces healthy levels of $O_2$ as supplied by blood to the choroid. This lack of $O_2$ initiates a cascade of events which begins with thinning of choroidal tissue and ends with symptomatic AMD. While there are some cases of AMD which are genetically related, we believe compromised blood flow acts to initiate and advance the disease in many non-genetic cases and may have a causative role in genetic AMD. We also postulate that the cause of both wet and dry AMD may be linked to reduced blood flow to the back of the eye. There is a literature precedent which establishes a link between Coronary Artery Disease (CAD) and AMD. While this link is well established in modern medical literature, until now, a direct link between supply of oxygen to the posterior ophthalmic vasculature and AMD has not been studied or established.

DETAILED DESCRIPTION OF THE INVENTION

The present invention is restoring and/or increasing the amount of oxygen that is available to one or more parts of the eye or to the eye area. Devices and methods are described.

Restoring and/or increasing the amount of oxygen is used herein to refer to any device, method, therapy, or combination that changes the oxygen content in or near the eye. Examples of such include, but are not limited to increasing the blood flow anywhere in the vasculature leading to the eye or a portion of the eye; removing or opening an obstruction in the fluid flow path in the vasculature leading to the eye; delivering and deploying a stent in the fluid flow path in the vasculature leading to the eye; using atherectomy or similar devices to physically remove portions of any obstructions in the vasculature leading to the eye or portion of the eye; and localized drug and/or an oxygen device for increasing flow or amount of oxygen in one or more eye tissues. In some an embodiments, a device or method of the present invention may be combined with a known or new drug or oxygen device in order to treat one or more eye diseases or conditions.

The present disclosure provides for an apparatus for deployment of a detachable diagnostic or therapeutic implant device such as a stent, embolic coil or other vascular occlusion device using a catheter, whereby placement of a stent or the like in a portion of the carotid artery changes the diameter of the internal carotid artery (ICA) and/or the ophthalmic artery (OA), which in turn increases blood flow between the ICA and the eye.

The present invention is restoring and/or increasing the amount of oxygen that is available to one or more parts of the eye or to the eye area, specifically by removing or partially opening a blockage in one or more of the arteries that supplies blood flow to the eye. In preferred embodiments of the invention, a blockage is removed or opened in the Internal Carotid Artery, the Ophthalmic Artery, the ostium (as used herein, referring to the junction between the ICA and the OA), or combinations thereof. In the most preferred embodiments, the devices and methods of the present invention involve increasing the blood flow and/or blood flow rate to or near the eye. To or near the eye, as used herein, refers to the vasculature system that supplies blood to the various structures of the eye.

Figure 4:
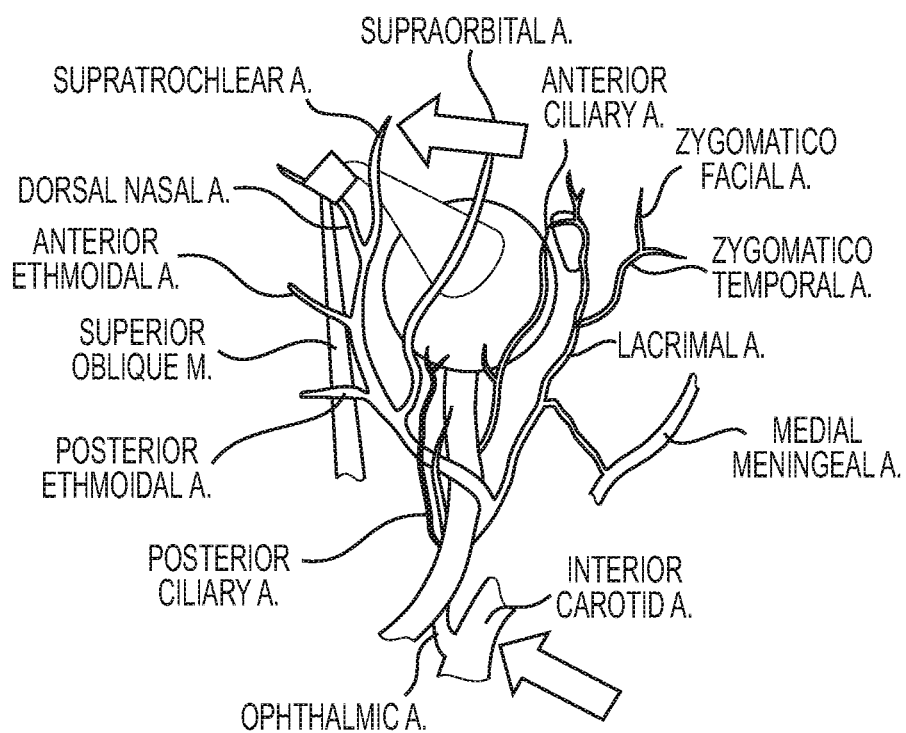
FIG. 4 is a representation of the vasculature between the internal carotid artery (ICA) and the eye.

The present invention includes methods, devices, and systems for removing a blockage in the ostium, wherein removing the blockage comprises opening a channel or access through the ostium sufficient to provide a therapeutically beneficial amount of oxygen to the eye, the rear of the eye, or portions thereof. The present invention also includes restoring and/or improving blood flow anywhere in the vascular pathway to or within the eye. FIG. 4 illustrates a portion of this vasculature. The top and bottom arrows show one embodiment of the invention, the vasculature pathway between the supratrochlear artery and the ostium of the ophthalmic artery and the internal carotid artery.

Another embodiment of the invention includes reducing and/or removing any blockage in the oxygen pathway to the eye. In this and other embodiments of the invention, reducing blockage includes but is not limited to piercing or penetrating the blockage. In most preferred embodiments of the invention, piercing and penetrating the blockage refers to obtaining sufficient blood and/or fluid flow through or around the blocked vascular area sufficient to provide a therapeutically beneficial amount of oxygen to the eye or a portion of the eye.

Another embodiment of the invention further includes supplying oxygen to the eye or near the eye, wherein, in this embodiment, the source of the oxygen is external.

Another embodiment of the invention includes one or more medical devices, such as a catheter or the like, and its use to clear or penetrate a blockage in the vascular system that provides oxygen to the eye. In preferred embodiments of the invention, the blockage in the vascular system and specifically is a blockage in the junction or connection between the ICA and the OA. In the present invention, this junction is termed the ostium.

Another embodiment of the invention includes a medical device, such as a stent or the like, that is configured for and may be used to open, clear, or improve vascular flow to or around the eye, wherein vascular flow mediates the amount of oxygen that is delivered to the eye.

Typically, these procedures involve inserting the distal end of a delivery catheter into the vasculature of a patient and guiding it through the vasculature to a predetermined delivery site. A vascular occlusion device may be attached to the end of a delivery member which pushes the occlusion device through the catheter and out of the distal end of the catheter into the delivery site.

For some of these embodiments, one or more layers of the implant device may be configured to anchor or fix the implant device in a clinically beneficial position. For some embodiments, the implant device may be disposed in whole or in part within the vascular defect in order to anchor or fix the device with respect to the vascular structure or defect. The one or more layers of the implant device may be configured to span an opening, neck or other portion of a vascular defect in order to isolate the vascular defect, or a portion thereof, from the patient's nominal vascular system in order to allow the defect to heal or to otherwise minimize the risk of the defect to the patient's health.

The invention also includes a delivery system configured or adapted to position and/or orient the stent in the ostium.

An embodiment of the inventions includes methods and devices for treating a non-human animal. Some embodiments of the invention include treating a dog, including but not limited to treating central serous retinopathy.

Some embodiments of a delivery system for deployment of an implant device to treat a patient's vasculature include a microcatheter having an inner lumen extending the length thereof. The inner lumen provides a passageway for an implant device to treat a patient's vasculature. Some implant device embodiments may include one or more self-expanding resilient layers of thin coupled filaments, the layers defining a longitudinal axis between a proximal end and a distal end. Such embodiments can assume a radially-constrained, axially-elongated state configured for delivery through a microcatheter, with the thin woven filaments extending longitudinally from the proximal end to the distal end being radially adjacent to each other. The delivery system further includes an elongated delivery apparatus having a proximal end and a distal end releasably secured to a proximal portion (e.g., a hub or the like) of the implant device.

Access to a variety of blood vessels of a patient may be established, including arteries such as the femoral artery, the radial artery, and the like, in order to achieve percutaneous access to a vascular defect. In general, the patient may be prepared for surgery, the access artery is exposed via a small surgical incision, and access to the lumen is gained using the Seldinger technique where an introducing needle is used to place a wire over which a dilator or series of dilators may dilate a vessel allowing an access sheath to be inserted into the vessel. This would allow the device to be used percutaneously. With an access sheath in place, a guiding catheter is used to provide a safe passageway from the entry site to a region near a treatment site. Exemplary guidewires for vascular use may include the Synchro2.® made by Boston Scientific and the Glidewire Gold Neuro® made by MicroVention Terumo. Typical guidewire sizes may include 0.014 inches (0.36 mm) and 0.018 inches (0.46 mm). Once the distal end of the microcatheter is positioned at the site, often by locating its distal end through the use of radiopaque marker material and fluoroscopy, the catheter is cleared. For example, if a guidewire has been used to position the microcatheter, it may be withdrawn from the microcatheter, and then the delivery apparatus may be advanced through the microcatheter.

Once the implant device is deployed at a desired treatment site, the microcatheter may then be withdrawn. Characteristics of the implant device and delivery apparatus discussed herein generally allow for retraction of the implant device after initial deployment into the vascular defect, but before detachment of the implant device. Therefore, it may also be possible and desirable to withdraw or retrieve an initially deployed implant device after the fit within the vascular defect has been evaluated in favor of a differently-sized implant device. The tip of a catheter, such as the microcatheter, may be advanced into or adjacent to the vascular site or vascular defect. An example of a suitable microcatheter having an inner lumen diameter of about 0.51 mm to about 0.56 mm is the Rapid Transit® manufactured by Cordis Corporation. Examples of some suitable microcatheters may include microcatheters having an inner lumen diameter of about 0.66 mm to about 0.71 mm, such as the Rebar® by Ev3 Company, the Renegade Hi-Flow® by Boston Scientific Corporation, and the Mass Transit® by Cordis Corporation. Suitable microcatheters having an inner lumen diameter of about 0.79 mm to about 0.84 mm may include the Marksmen® by Chestnut Medical Technologies, Inc. and the Vasco 28® by Balt Extrusion. A suitable microcatheter 61 having an inner lumen diameter of about 1.0 mm to about 1.04 mm includes the Vasco 35® by Balt Extrusion. These microcatheters are listed as exemplary embodiments only, and other suitable microcatheters may also be used with any of the embodiments discussed herein.

Applicants and inventors intend that the invention should not be limited solely to changing vascular flow in order to improve or restore the amount of oxygen that is delivered to the eye. For example, in some embodiments of the invention, the vascular flow may be unaffected for the most part, but the amount or concentration of hemoglobin may be increased, thereby increasing the amount of oxygen that may be delivered to the eye. One skilled in the art may recognize, with the teaching of this invention, that there are other biological systems or capabilities that may be used to increase the amount of oxygen that is delivered to the eye.

In accordance with the present invention, any process, device, or agent that increases the availability of oxygen to the eye or eye region is included within the scope of the present invention. These processes, devices, and agents include, but are not limited to internal sources of oxygen, e.g., through the vascular system. These processes, devices, and agents include, but are not limited to external sources of oxygen, e.g., an injection into the eye or eye region with one or more substances that carries oxygen, a substance that captures or concentrates oxygen, a device that manufactures oxygen and/or one of more substances that result in an increase the amount of oxygen.

Figure 1:
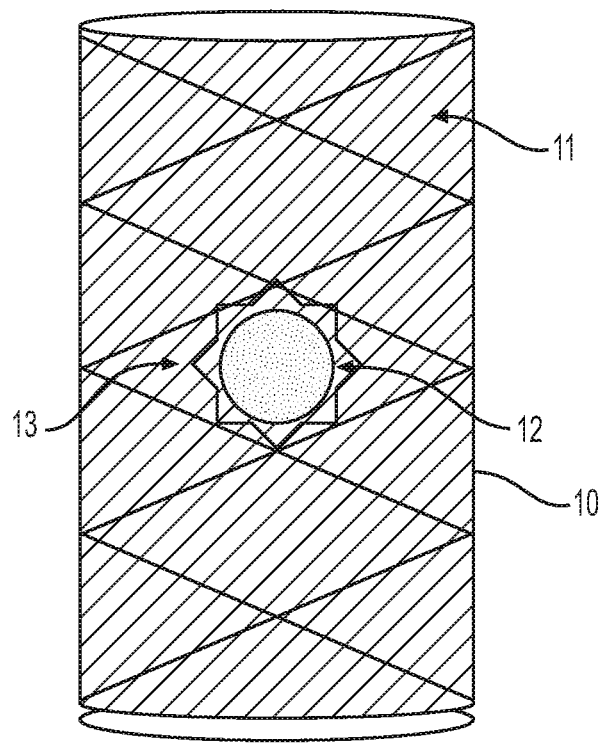
FIG. 1 provides an exemplary design for a stent of the present invention.
Figure 2:
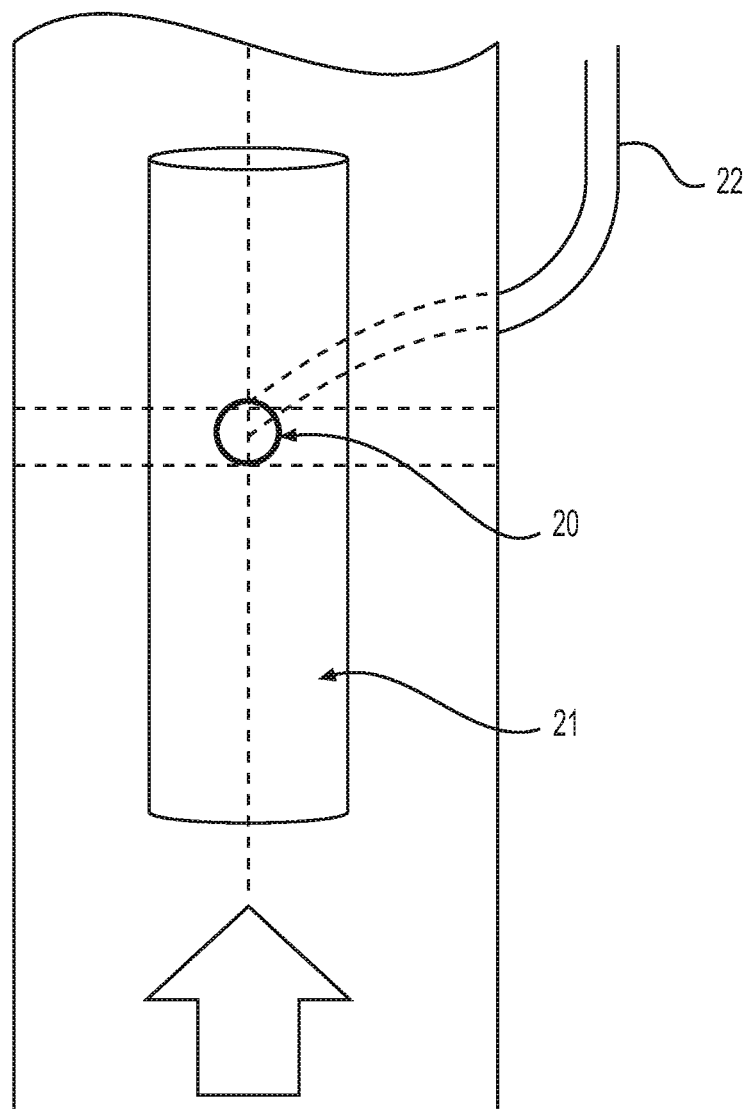
FIG. 2 shows a possible placement of the stent in the ICA.
Figure 3:
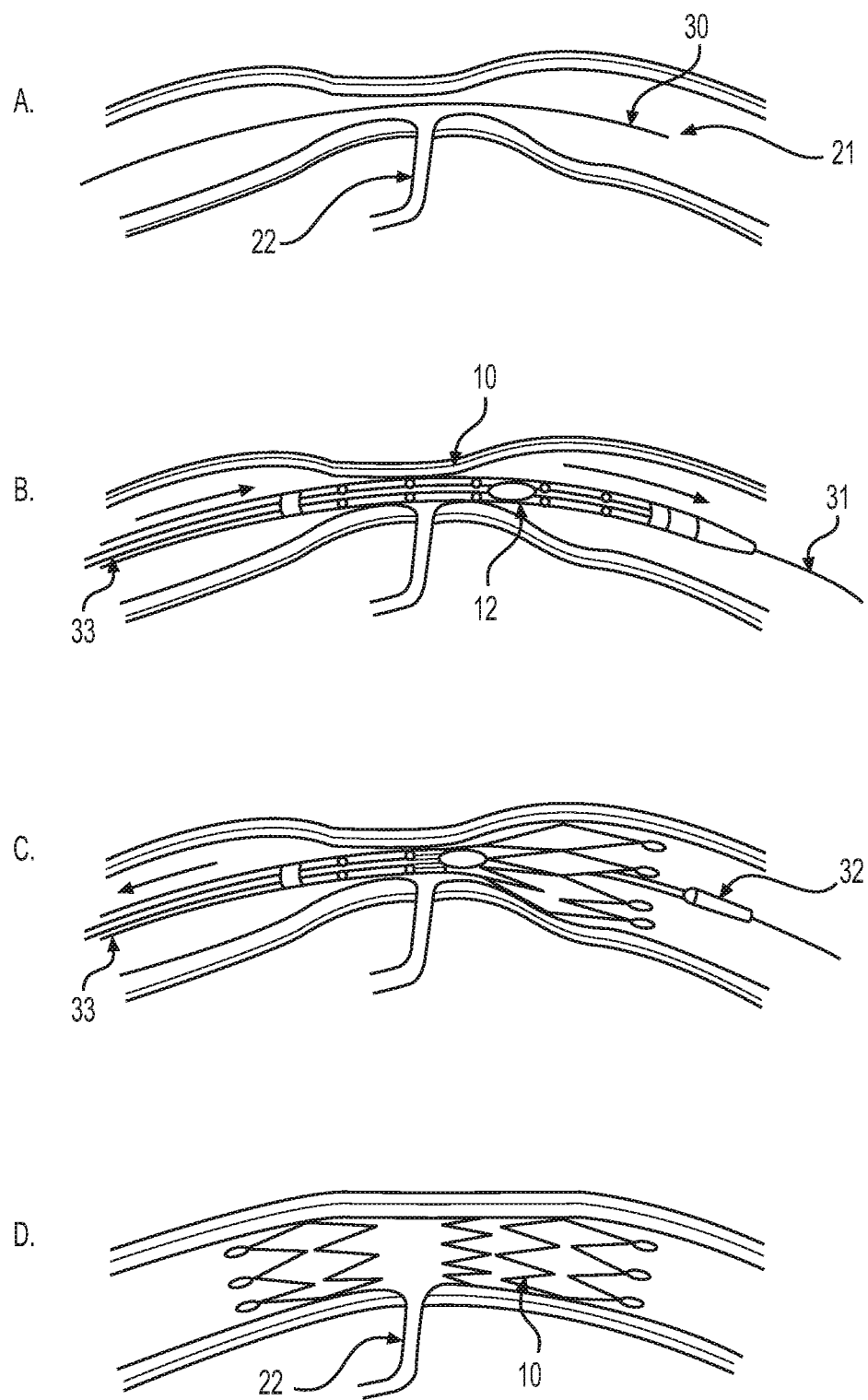
FIG. 3 illustrates the delivery steps for deploying a stent in the ostium.

In some embodiments of the invention, the invention includes a stent, adapted and configured to be delivered to any predetermined area in the vascular system that supplies oxygen to the eye, e.g., the internal carotid artery (ICA). In preferred embodiments of the invention, the stent, e.g., stent 10 shown in FIGS. 1-3, is adapted and configured for placement in the ICA/ophthalmic artery ostium.

A stent of the present invention may be configured for placement in the vasculature supplying blood to the eye. Exemplary blood vessels include but are not limited to the arteries shown in FIG. 4, the internal carotid artery, and the ophthalmic artery. A stent may also be configured or adapted for treating an obstruction of the Ophthalmic/Internal Carotid Artery ostium, comprising: stent ranging in diameter from about 2.5 mm to about 5.5 mm, with an overall length ranging between 15 mm to 40 mm. The stent may have a tapered diameter to facilitate placement within the vasculature. The stent may be self-expanding, non-expanding, or expandable. In embodiments of the invention in which the stent is expandable, the stent may be expanded using any known expanding element, e.g., a balloon or the like. In preferred embodiments of the invention, the stent is percutaneously delivered.

The present invention is also a system comprising a stent and its delivery apparatus; said system is used for increasing the amount of oxygenated blood in the eye area.

A system of the present invention includes a stent configured for placement and function in the ostium; a catheter for delivering the stent to the ostium or near the ostium, and any of a number of already known structures and devices typically delivered by catheter.

A stent 10 of the present invention may be constructed from materials commonly used in the design and manufacture of self-expanding stents. These materials include, but are not limited to, Nitinol, chromium cobalt, stainless steel, polymers, bioresorbable and/or other materials commonly used in the coronary vasculature.

The stent may also include a cover 11. The covering could be on the inner diameter, the outer diameter, some combination of location specific (strut or struts). It could be a fabric like covering, liquid or a degrading material.

In some embodiments of the invention, the cover may function to trap particulate in and around the stent area. In this embodiment of the invention, the covering is believed to reduce the potential for inducing thrombosis. In other embodiments of the invention, the stent may include one or more anti-stenosis agents. In other embodiments, the stent may include both functions.

The cover may be formed from PTFE or other commonly used material designed to be affixed to the outer diameter of the stent with the purpose of providing a method of retaining plaque (or stenotic material) as the stent is expanded against the artery. This covering material is designed to expand with the stent and trap material potentially loosened by the dilatation effect of the stent between the covering and the vascular wall.

The stent or the cover may also include one of more markers, typically radiopaque markers. The stent or cover may be coated or impregnated with one or more radiopaque markers 13 to aid in the proper placement of the stent within the target anatomy, e.g., the ostium 20 of the ICA 21 and the OA 22. Target anatomy, as used herein, refers to any place in the vascular system supplying blood to the eye, including but not limited to the ostium of the ICA and OA.

In preferred embodiment the stent covering is designed to provide an opening for accommodation of the Ophthalmic Artery (OA) ostium such that the material does not block access to the OA ostium. In preferred embodiments of the invention, the opening is an area of the stent that is free of stent struts and is unobscured by the stent covering. Exemplary openings are shown in the figures.

The stent may comprise an opening or port 12 on the circumference that is free from stent struts and is unobscured by the stent covering. This opening is dimensionally compatible with the opening of the OA at the ostium such that the OA will be unobscured by the device once it is placed within the vasculature.

In a preferred embodiment the stent is designed with a section that contains a structure capable of providing intraluminal support without blocking the OA ostium. This section may be referred to as a window or opening. In this embodiment, the window of the stent mirrors that of the opening designed into the stent covering material, if a covering material is used. The windows of the stent and the stent covering are configured to correspond or align with complementary markers integrated into the delivery catheter. These markers are designed to facilitate proper placement of the stent within the anatomy such that the OA ostium is not blocked by the stent/stent covering material.

In another preferred embodiment, the stent is disposed within a delivery catheter and sheath, said catheter having a means of providing a single radiopaque marker or plurality of radiopaque markers to aid in the positioning the stent in the appropriate anatomical location within the target anatomy.

In another preferred embodiment, the stent is designed to deploy (e.g., via self-expansion) such that the distal portion of the stent deploys first and aids in anchoring the device prior to deployment of the proximal section of the stent. This is necessary so as to provide the physician with the ability to accurately place the stent within the target anatomy. The stent is first placed in the desired location and then fully delivered.

In another preferred embodiment, the stent is designed with an asymmetrical feature that exerts additional diametric force in the area of the OA ostium.

The stent of the present invention may be delivered using any medically appropriate route and/or technique. Suitable routes include but are not limited to subclavian, brachial, and/or direct common carotid access. In a preferred embodiment, the device and system is configured for percutaneous access of the Internal Carotid Artery (ICA) via a femoral approach as well as other typical percutaneous access locations.

In another preferred embodiment, the system is configured to be used with commonly available coronary guide wire products in styles and size ranges.

A stent or cover of the present invention may be configured to be visible using non-invasive imaging techniques (i.e.: fluoroscopy). In this embodiment of the invention the stent and/or cover may include one of more elements to assist in positioning and deploying the stent.

In another preferred embodiment, the method consists of several components, including a delivery catheter with the stent mounted on a central catheter 32 by means of an outer sheath that compresses and holds the stent against the central portion of the catheter to aid in the delivery of the stent to the desired anatomy. In FIG. 3A, the central portion of the catheter incorporates a through lumen intended to facilitate the use of a guide wire 30 to aid in positioning the device within the target vasculature. Once proper placement is achieved, the guide wire is removed and replaced with a filter wire 31. In FIG. 3B, the filter wire is deployed such that the optional filtering capability is placed distal to the OA ostium and outside of the field of stent deployment. Once in the proper position, the filter element may be deployed such that filtering capability is provided. The stent is then manipulated via the radiopaque markings such that the OA ostium will not be obscured by the stent. The stent is then deployed by slowly retracting the delivery sheath 33. In FIG. 3C, retracting the delivery sheath is aided by radiopaque markings on the sheath as well as markings on the stent. The distal portion of the stent is placed first to ensure the OA ostium will not be blocked. Once the stent is in place, observation of a non-blocked ostium is confirmed and the proximal portion of the stent is delivered, the filter wire and any captured debris is withdrawn into the delivery catheter and the system removed. FIG. 3D shows an embodiment of the invention in which the stent 10 is positioned in the ICA with the port aligned with the junction between the ICA and the OA 22.

The present invention is also a system comprising one or more medical devices, (e.g., a stent) and its delivery apparatus; said system is used for increasing the amount of oxygenated blood in the eye area, or for increasing the amount of oxygen that is or can be delivered to the eye. The invention may also include this system, device, or method in combination with one or more agents or devices for improving vascular blood flow between the common carotid artery and a central artery of the retina; one or more agents for improving vascular blood flow at the ostium and within the OA.

In some embodiments of the invention, the delivery system contains a sheath used to compress the stent on the central catheter. Controlled removal of the sheath provides for the ability to deliver the stent to the desired anatomical location. The sheath may include a mechanical element to allow for controlled advancement and/or retraction of the stent. The sheath will also have radiopaque markings to aid in the positioning and delivery of the stent The invention further includes the use of one of more diagnostic devices or agents that allow a person to monitor oxygen content in the eye.

In another embodiment, a medical device or agent is capable of delivering drugs to the ostium for the purpose of improving vascular blood flow at the ostium and within the OA. These drugs may include (but are not limited to) low dose Viagra (or equivalent RPE inhibitor), Lucentis, Avastin, Taxol, Rapamyacin or other pharmaceuticals used to improve vascular blood flow.

In one embodiment, the ophthalmological disease or disorder treated or prevented by any of the methods or compositions described herein is age-related macular degeneration. Vision changes that can be associated with macular degeneration include distortions and/or blind spots (scotoma) detected using an Amsler grid, changes in dark adaptation (diagnostic of rod cell health), changes in color interpretation (diagnostic of cone cell health), or a decrease in visual acuity. Examples of age-related macular degeneration are normeovascular (also known as "dry") and neovascular (also known as "wet" or "exudative") macular degeneration.

In one embodiment, the dry age-related macular degeneration is associated with the formation of drusen. In one embodiment, treating or preventing dry macular degeneration encompasses treating or preventing an abnormality of the retinal pigment epithelium and/or underlying vasculature, known as choriocapilaries. Examples of abnormalities of the retinal pigment epithelium include geographic atrophy, non-geographic atrophy, focal hypopigmentation, and focal hyperpigmentation. In another embodiment, treating or preventing wet age-related macular degeneration encompasses treating or preventing choroidal neovascularization or pigment epithelial detachment.

In some embodiments, wet age-related macular degeneration is classified according to the appearance of its choroidal neovascularization (CNV), into classic, occult or mixed (classic and occult) CNV types, as determined by an angiography, known as fluorescence angiography. Classic, occult or mixed (classic and occult) CNV classification can be based on the time, intensity and level of definition of dye appearance, and leakage from the CNV, as assessed by the fluorescein angiography. In some embodiments, the subject has classic CNV (e.g., pure classic) or mixed CNV (predominantly or minimally classic CNV). In some embodiments, the subject has occult CNV (e.g., pure occult CNV).

In certain embodiments, the ophthalmological disease or disorder is a cataract (e.g., age-related cataract), diabetic macula edema, macular telangiectasia (e.g., type 1 or 2 macular telangiectasia), atrophic macular degeneration, chorioretinopathy (e.g., central serous chorioretinopathy), retinal inflammatory vasculopathy, pathological retinal angiogenesis, age-related maculopathy, retinoblastoma, Pseudoxanthoma elasticum, a vitreoretinal disease, choroidal sub-retinal neovascularization, central serous chorioretinopathy, ischemic retinopathy, hypertensive retinopathy or diabetic retinopathy (e.g., nonproliferative or proliferative diabetic retinopathy, such as macular edema or macular ischemia), retinopathy of prematurity (e.g., associated with abnormal growth of blood vessels in the vascular bed supporting the developing retina), venous occlusive disease (e.g., a retinal vein occlusion, branch retinal vein occlusion or central retinal vein occlusion), arterial occlusive disease (e.g., branch retinal artery occlusion (BRAO), central retinal artery occlusion or ocular ischemic syndrome), central serous chorioretinopathy (CSC), cystoid macular edema (CME) (e.g., affecting the central retina or macula, or after cataract surgery), retinal telangiectasia (e.g., characterized by dilation and tortuosity of retinal vessels and formation of multiple aneurysms, idiopathic JXT, Leber's miliary aneurysms, or Coats' disease), arterial macroaneurysm, retinal angiomatosis, radiation-induced retinopathy (RIRP), or rubeosis iridis (e.g., associated with the formation of neovascular glaucoma, diabetic retinopathy, central retinal vein occlusion, ocular ischemic syndrome, or chronic retinal detachment).\

Human blood vessels often become occluded or blocked to the extent that the blood carrying capacity of the vessel is reduced. Should the blockage occur at a critical place in the circulatory system, serious and permanent injury can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, and thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically comprises a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Embodiments of the present invention and the various components or elements thereof can be used interchangeably so that features and functions of one exemplary embodiment of a filter device can be used with other embodiments of the filter device. Illustratively, the restraining members or mechanisms of the described embodiments of the present invention can be used with multiple different configurations of the filter device. Further, exemplary capture catheters can be used interchangeably such that any capture catheter can be used with any of the described filter devices and such other that may be known to those skilled in the art in light of the teaching contained herein. Additionally, methods of using one embodiment of the present invention can be used with other embodiments of the present invention. Therefore, embodiments of the present invention provide filter devices that have small, low, or no profiles, few parts and components, are simple to manufacture and use, are able to be easily inserted into a patient, be steerable through the tortuous anatomy of a patient, provide filtering capabilities, provide exchange capability so other medical devices can be advanced over or along the filter device, and be capable of removing captured material without allowing such material to escape during filter retrieval.

EXAMPLES

Example 1

The inventors believe that compromised blood flow to the vasculature of the posterior eye directly contributes to diseases of the eye. This lack of normal blood flow may originate in the internal carotid artery (ICA), the ophthalmic artery (OA), branches of the ophthalmic artery and/or combinations thereof and be directly caused by a blockage in one or more of these vessels. This lack of sufficient blood flow directly contributes to inadequate oxygen levels seen in tissues such as the choroid, retina, optic nerve and other ophthalmic anatomy. This blockage may manifest as stenosis, lesions or other physiology within the ophthalmic related vasculature and compromise normal blood flow such that the posterior eye vasculature does not receive an adequate oxygen supply for maintenance of normal function. As a result of this reduction of oxygen, it is possible for a cascade of events to begin which may result in various diseases of the eye.

Blood flow was measured for healthy controls and diseased patients (with confirmed AMD diagnosis). Flow rates were measured for the Left Ophthalmic Artery (LOA), Right Ophthalmic Artery (ROA), Left Internal Carotid Artery (LICA) and Right Internal Carotid Artery (RICA) using Phased Contrast Magnetic Resonance Imaging (PCMRI) technique. These flow rates were measured in cm/sec. The average size of the ICA was 4.66 mm and the average size of the OA was 1.00 mm.

Specific flow rates were compared, and the OA flow data shows a medically or clinically observable difference between the flow rates for healthy controls compared to diseased patients. Specific flow rates were compared, and the ICA flow data shows a medically or clinically observable difference between the flow rates for healthy controls compared to diseased patients. In every case, the blood flow rate for the diseased patients appears to be lower than the blood flow rate for the healthy controls.

Example 2

We obtained cadaveric tissue samples, with confirmed diagnosis of CAD with no diagnosis of AMD. We were able to visually confirm presence of stenosis in the ophthalmic/internal carotid ostium of the samples. One sample had extensive stenosis that appeared to completely block the OA in both the left and right ICA/OC ostiums. It should be noted that the left OA, as observed branching off the ICA, was much smaller in diameter than that of a typical OA, almost to the point of being non-existent. This sample was diagnosed with CAD, CHF, PAD, HTN and 4× bypass Sx.

A different sample had what appeared to be early stage stenosis accumulation in both the left and right ICA/OA ostiums as confirmed by visual observation. None of these stenosis appeared to cause blockage in the OA of either ostium. This sample was diagnosed with CAD, chronic anemia, Buerger's disease, Thromboembolic disease and extensive DVT.

Example 3

In another sample we then removed the right ICA and visually examined the ostium. We confirmed blockage of the OA at the ostium which appeared to be complete. Once the section of left ICA was removed, we were able to gain internal access to the OA ostium and insert a micro PTCA balloon catheter. We performed this test to visually observe the effect of placing and inflating a balloon catheter in the OA. This (non-compliant) balloon catheter has a maximum diameter of 0.85 mm at 16 atms, with a crossing profile of 0.74 mm and a working length of approximately 5 mm. We inflated the balloon several times to approximately 12 atms max and observed the balloon through the vessel. The vessel appeared to tolerate the inflations without obvious damage.

We claim:

1. A method for treating an eye disease, condition, or disorder in a diseased blood vessel of an eye of a subject, the method comprising:
    increasing an amount of oxygen available to the diseased blood vessel of the eye, the increasing the amount of oxygen comprising:
    inserting a stent into an artery of the subject from which the diseased blood vessel branches, the stent having a side opening between a distal end and a proximal end thereof;
    positioning the side opening of the stent over an ostium between the artery and the diseased blood vessel of the subject; and
    deploying the stent.

2. The method of claim 1, wherein a diameter of the stent is from 2.5 mm to 5.5 mm, and an overall length of the stent is from 15 mm to 40 mm.

3. The method of claim 1, wherein the stent has a tapered diameter.

4. The method of claim 1, wherein the stent is self-expanding.

5. The method of claim 1, wherein the stent comprises one or a combination of Nitinol, chromium cobalt, stainless steel, polymer, or a bioresorbable material.

6. The method of claim 1, further comprising:
    removing material from the diseased blood vessel via an atherectomy procedure.

7. The method of claim 1, wherein deploying the stent comprises deploying a distal portion of the stent prior to the positioning the side opening step, and deploying a proximal portion of the stent after the positioning the side opening step.

8. The method of claim 1, wherein the artery is an internal carotid artery and the diseased blood vessel is an ophthalmic artery of the subject.

9. The method of claim 8, wherein deploying the stent includes increasing a diameter of the internal carotid artery.

10. The method of claim 1, further comprising delivering one or more pharmaceutical agents via the stent.

11. The method of claim 1, wherein positioning the side opening of the stent over the ostium includes observing if blood flow between the artery and the diseased blood vessel via the ostium is maintained or initiated.

12. A method of treating an eye condition of an eye of a subject, the method comprising:
    advancing a stent within an internal carotid artery of the subject to a delivery site, the stent including a plurality of struts and a side-wall opening positioned between a distal end of the stent and a proximal end of the stent;

deploying the distal end of the stent distally of an ostium between the internal carotid artery and an ophthalmic artery of the subject;

after deploying the distal end of the stent, manipulating the stent so that the side-wall opening of the stent is aligned with the ostium; and after the manipulating the stent, deploying the proximal end of the stent proximally of the ostium.

13. The method of claim 12, wherein a diameter of the stent is from 2.5 mm to 5.5 mm, and an overall length of the stent is from 15 mm to 40 mm.

14. The method of claim 12, wherein the stent has a tapered diameter.

15. The method of claim 12, wherein the stent is self-expanding.

16. The method of claim 12, wherein the stent comprises one or a combination of Nitinol, chromium cobalt, stainless steel, polymer, or a bioresorbable material.

17. The method of claim 12, wherein the manipulating the stent includes observing if blood flow between the internal carotid artery and the ophthalmic artery via the ostium is maintained or initiated.

18. The method of claim 12, wherein a central longitudinal axis extending through the side-wall opening is transverse to a central longitudinal axis extending between the proximal end and the distal end of the stent.

19. The method of claim 12, further including deploying a filter distal of the stent.

20. A method of treating an eye condition of an eye of a subject, the method comprising:

advancing a stent within an internal carotid artery of the subject to a delivery site, the stent including a plurality of struts and a side-wall opening positioned between a distal end of the stent and a proximal end of the stent, wherein a central longitudinal axis extending through the side-wall opening is transverse to a central longitudinal axis extending between the proximal end and the distal end of the stent;

deploying the distal end of the stent distally of an ostium between the internal carotid artery and an ophthalmic artery of the subject;

after deploying the distal end of the stent, manipulating the stent so that the side-wall opening of the stent is aligned with the ostium, wherein the manipulating the stent includes adjusting a location of the distal end of the stent;

observing if blood flow between the internal carotid artery and the ophthalmic artery via the ostium is maintained or initiated; and after the manipulating the stent, deploying the proximal end of the stent proximally of the ostium.

* * * * *